(12) United States Patent
Blees et al.

(10) Patent No.: US 7,692,136 B2
(45) Date of Patent: Apr. 6, 2010

(54) PORTABLE ILLUMINATION DEVICE

(75) Inventors: Martin Hillebrand Blees, Eindhoven (NL); Ferry Barrois, Eindhoven (NL); Wilhelmus Frederik Laurens Maria Hoeben, Eindhoven (NL); Mikhail Sorokin, Eindhoven (NL); Ludo Haenen, Eindhoven (NL); Bennie Simpelaar, Eindhoven (NL); Nebojsa Fisekovic, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 12/279,074

(22) PCT Filed: Feb. 15, 2007

(86) PCT No.: PCT/IB2007/050499

§ 371 (c)(1),
(2), (4) Date: Aug. 12, 2008

(87) PCT Pub. No.: WO2007/096814

PCT Pub. Date: Aug. 30, 2007

(65) Prior Publication Data

US 2009/0014624 A1  Jan. 15, 2009

(30) Foreign Application Priority Data

Feb. 20, 2006  (EP) ................................. 06110151

(51) Int. Cl.
*H01J 3/14* (2006.01)
*G01J 1/32* (2006.01)
*F21L 4/02* (2006.01)

(52) U.S. Cl. ........................ 250/216; 250/205; 362/184

(58) Field of Classification Search ................. 250/216, 250/221, 552, 559.46, 564, 573–575, 577, 250/204, 205; 362/184, 187, 205
See application file for complete search history.

(56) References Cited

U.S. PATENT DOCUMENTS

| | | | |
|---|---|---|---|
| 4,470,680 A * | 9/1984 | Inagaki ........................ 396/28 |
| 6,488,390 B1 | 12/2002 | Lebens et al. |
| 6,496,471 B1 | 12/2002 | Sato et al. |
| 6,936,978 B2 | 8/2005 | Morgan et al. |
| 2003/0085849 A1 | 5/2003 | Grabert |
| 2003/0095406 A1 | 5/2003 | Lebens et al. |
| 2004/0223320 A1 | 11/2004 | Archer et al. |
| 2005/0040773 A1 | 2/2005 | Lebens et al. |
| 2005/0047125 A1 | 3/2005 | Puckett |
| 2005/0091905 A1 | 5/2005 | Larson et al. |
| 2005/0099798 A1 | 5/2005 | Cugini et al. |
| 2005/0099799 A1 * | 5/2005 | Cugini et al. ............... 362/105 |

FOREIGN PATENT DOCUMENTS

| | | |
|---|---|---|
| DE | 3340014 A1 | 6/1985 |
| DE | 4316691 A1 | 11/1994 |
| JP | 2001228517 A | 8/2001 |
| WO | 02101777 A2 | 12/2002 |

* cited by examiner

*Primary Examiner*—Georgia Y Epps
*Assistant Examiner*—Don Williams

(57) ABSTRACT

A portable illumination device, for illuminating an object through a medium having an absorption coefficient, has a lighting unit including at least two differently colored light sources for emitting light having a color distribution and a control unit for adjusting the color distribution. The control unit is adapted to receive a distance estimate corresponding to the distance between the illumination device and the object, and adjust the color distribution depending on the distance estimate, such that light reflected from the object is perceived to have substantially correct color reproduction.

24 Claims, 3 Drawing Sheets

PORTABLE ILLUMINATION DEVICE

The present invention relates to a portable illumination device, and more particularly to a portable underwater dive light.

For example, when performing deep diving and when diving during the night, the use of a dive light is essential. Additionally, during daytime recreational diving the use of a dive light is also essential in order to be able to see the vivid colors of aquatic life. Without such a light, all underwater scenery will look grayish blue already at a moderate depth of for example 15 meters. Two of the most important aspects when choosing a dive light are the depth rating and the burn time. The depth rating generally depends on certain devices such as double o-rings and magnetic switches which make the dive light more reliable under pressure, whereas the burn time generally depends on the power consumption of the light sources in combination with the capacity of the battery used in the dive light.

Conventional incandescent halogen light bulbs generally have a very inefficient yielding and deliver at best only about 6% of their electric power used in the form of light. However, light emitting diodes (LEDs) today have an energy efficiency that is much higher. As a result, LEDs have become sufficiently bright, inexpensive, and energy efficient to serve as a light source in for example portable illumination devices, such as dive lights. When diving, it is generally desired to use a white light source. Prior art discloses two main ways of creating white light using LEDs. The first way is by mixing differently colored LEDs, for example three differently colored LEDs of the color primaries red, green and blue. By turning on all three differently colored LEDs at the same time, "white" light is generated. The second known way is by coating a blue LED with phosphor. The phosphor acts as a wavelength converter, converting part of the light to longer wavelength, thereby generating "white" light.

A flashlight for use as an underwater dive light is disclosed in US 2005/0047125. In one embodiment, the light sources are LEDs. However, the use of normal narrow banded LEDs will fail to provide a correct color reproduction when illuminating an object under water. This is due to the absorption spectrum of water. The absorption of light in water depends on wavelength and is due to absorption and scattering by molecules and particles. Blue light is absorbed least and red light is absorbed most strongly. As can be seen in FIG. 3, the absorption coefficient of red light is at least 100 times higher than blue light.

There is therefore a need for a portable illumination device and a method for illuminating an object in a medium, substantially overcoming at least some of the disadvantages of the prior art, and more specifically that overcome the problems with red light absorption when illuminating an object under water.

According to an aspect of the invention, there is provided a portable illumination device for illuminating an object through a medium, the medium having an absorption coefficient and being able to absorb a portion of the visible light spectrum, said illumination device comprising a lighting unit including at least two differently colored light sources for emitting light having a color distribution, and a control unit for adjusting said color distribution. The control unit is adapted to receive a distance estimate corresponding to the distance between said illumination device and said object, and adjust said color distribution depending on said distance estimate, such that light reflected from said object is perceived to have substantially correct color reproduction.

Light traveling a certain distance through gas, liquid or solid matter is attenuated by absorption. Absorption is the process of converting light into thermal energy (heat motion of the molecules). The effect of absorption of light under water is described in U.S. Pat. No. 6,936,978, where also variation of a red light source in order to overcome the absorption is discussed. However, this document relates to an apparatus for providing coordinated illumination effects of water in a pool or a spa environment. The light source is thus permanently installed, and its light settings are adapted upon installation so that the emitted light results in the intended effect when someone looks in the pool. The present invention is instead intended to be portable, and to illuminate objects on varying distances from the device. The purpose is not to provide lighting effects, but to provide a correct color reproduction of an object when the visible light spectrum is distorted, e.g. when a portion of the visible light spectrum is absorbed.

According to the invention, it is thus possible to adjust the color distribution of the light emitted by the at least two light sources, i.e. the spectral power distribution of the light emitted by the portable illumination device, according to the distance to the object such that the color reproduction of the light that is reflected back from the object to the portable illumination device is perceived as substantially correct. An advantage with the invention is that an object illuminated through a medium will be perceived by a user using the portable illumination device as having a substantially correct color reproduction. That is, the reflected light will have a substantially correct colour reproduction only when reaching the eyes of the user.

In the absorption process light disappears, and the amount of absorption varies with wavelength of the incident light. If the composition of the medium through which the light propagates is uniform, the attenuation of the light intensity is described by exponential decay and characterized by an absorption coefficient. Preferably, the adjustment of the color distribution is therefore based on the absorption coefficient of the medium.

According to an embodiment of the invention, the control unit is adapted to adjust the color distribution by adjusting relative intensities of said light sources. This can be achieved by for example adjusting the time the light sources are turned on in a pulse-width modulated manner, or adjusting the amount of voltage/current provided to the light sources. However, the person skilled in the art realizes that it would be possible to adjust the color distribution by using for example adjustable color filters.

Preferably, one of the at least two differently colored light sources comprises at least one red light source. This is due to the fact that many liquids have a higher absorption of light within the red part of the visible light spectrum. By providing at least one red light source it is thereby possible to handle large absorptions of red light, for example due to a long distance between the portable illumination device and the object to be illuminated.

In a preferred embodiment of the present invention, the lighting unit comprises at least three differently colored light sources including at least one red light source, at least one green light source, and at least one blue light source. By mixing differently colored light, any number of colors can be generated, e.g. white. An adjustable color lighting system is typically constructed by using a number of primary colors, such as for example the three primaries red, green and blue. The color of the generated light is determined by the light emission spectrum of the sources that are used, as well as by the mixing ratios. To generate "white", all three light sources have to be turned on, and by using at least three differently colored light sources it is possible to adjust the individual intensities of the light sources such that the illuminated object is seen having a substantially correct color reproduction. However, it would be possible to only adjust the intensity of the red light source and keep the other differently colored light sources at a fixed intensity level.

To achieve a high energy efficiency and a longer battery time the light sources are preferably selected from a group comprising light emitting diodes (LEDs), organic light emitting diodes (OLEDs), polymeric light emitting diodes (PLEDs), inorganic LEDs, cold cathode fluorescent lamps (CCFLs), hot cathode fluorescent lamps (HCFLs), plasma lamps. As mentioned above, LEDs have a much higher energy efficiency in comparison to conventional light bulbs which generally deliver at best about 6% of their electric power used in the form of light. The skilled person would appreciate that it of course would be possible to use a standard incandescent light source, such as an argon, krypton, and/or xenon light source.

In an embodiment of the present invention, the distance estimate (i.e. the distance from the portable illumination device to the object to be illuminated) is estimated by a user and provided through a user interface. The user interface can for example be arranged as a rotatable switch adapted to provide predefined distance estimates depending on the setting of the switch. The switch can for example have five setting, preset to five distance estimate, e.g. 1 meter, 2 meters, 4 meters, 7 meters, and 10 meters. A person skilled in the art understand that it would be possible to have a more complex graphical user interface through which the user can provide a more exact distance estimate.

In an alternative embodiment of the present invention, the portable illumination device further comprises distance measuring electronics adapted to provide the distance estimate, which in this case can be more accurate. The distance measurement electronics can for example be constituted by time of flight sensors, which derives a distance measurement from the time it takes light to travel from the sensor to the object and return. In this case it is necessary to take into account the fact that light travels slower in a liquid than in air. Laser based rangefinders using pulsed laser beams or ultrasonic devices may also be used.

The portable illumination device is preferably arranged as a waterproof underwater dive light. In this case, the lighting unit can constitute a first waterproof compartment, the control unit can be arranged in a second waterproof compartment having an electrical connection to said first compartment, and the first compartment and the second compartment can be arranged relatively to each other such that, in use, water comes in contact with an exterior surface of the first compartment such that heat generated by the light sources is effectively absorbed by the water. This allows the use of high power light sources generating significant heat, such as high power LEDs, as the generated heat is advantageously absorbed by the water due to the design of the dive light. In this way the junction temperature of the LEDs is kept at a low level, ensuring efficient light output. Furthermore, it is possible to manufacture the first and the second compartment separately of each other, for example in different materials, and arrange the bodies in such a relation to one another such that more of the exterior of the lighting unit comes in contact with the water (in comparison to if the illumination device was constituted by a single compartment), thereby providing for a more efficient absorption of the heat generated by the light sources. However, the skilled person understands that it would be possible to design the portable illumination device as one compartment, where the compartment is adapted such that the above described water absorption effect is substantially obtained. Furthermore, the exterior surface of the first compartment is preferably formed by a material having a high thermal conductivity, wherein the light sources are arranged in thermal connection with said material. This provides for an even more efficient transport of the heat generated by the light sources to the surrounding liquid.

Preferably, the portable illumination device further comprises a water detector adapted to provide a water detection signal, and the control unit is further adapted to receive the water detection signal, and adjust the light intensities based on the water detection signal. For instance, such a water detection signal can be provided by measuring the resistance, the capacitance, or both between two separate electrical contacts that are located on the exterior surface of the first compartment. By means of the water detector, it is possible to limit the intensities of the light sources in the case that no water is detected, such that the light sources do not overheat due to the lack of water cooling.

To further improve the accuracy of the color reproduction in the light reflecting from the illuminated object, the portable illumination device can comprise light absorption characteristics electronics adapted to provide wavelength dependent absorption data of the surrounding medium. In this case, the control unit is further adapted to receive said absorption data, and adjust said light intensities based on said absorption data. For instance photodiodes with different color filters can be provided in combination with a low intensity broadband light source of known characteristics at a known distance from the photodiodes to provide absorption data of the medium for input into the control unit. Alternatively, instead of the broadband light source several small band light sources such as LEDs may be driven in a pulsed way to deliver light that is attenuated by the surrounding medium to a photodiode to provide absorption data for the control unit. For accurate measurement, it may be required to shield such a unit from other sources of light such as daylight. The control unit will in this case be further adapted to receive and process this absorption data, and accordingly adjust the light intensities. The light absorption in for example water also depends on various pigments with different light absorption characteristics, such as different phytoplankton. By measuring light absorption characteristics of the liquid, it is possible to achieve an improved accuracy of the color reproduction of the reflected light, as both the distance to the object and the light absorption characteristics are taken into account when adjusting the relative intensities of the differently colored light sources.

To even further improve the accuracy of the color reproduction in the light reflecting from the illuminated object, the portable illumination device can comprise electronics to measure the intensity and color spectrum of the daylight at the depth of the portable illumination device. The measurements are processed in the control unit in order to adjust the output color of the illumination device such that the color reproduction of the illuminated objects is optimized. The input signal from a distance sensor can also be fed into the control unit allowing the calculation of the relative intensity of the light supplied by the portable illumination unit (that decreases quadratically with the distance from the light source) and the daylight at the approximate depth of the object, and subsequent adjustment of the relative light output of the different color light sources to take into account the intensity and color of the daylight.

The invention is furthermore advantageously used as a component in for example, but not limited to, a camera arrangement. Such a camera arrangement can comprise a camera, such as a photo camera or a video camera, where the camera comprises a distance/focus sensor, and a portable illumination device as described above. The distance/focus sensor in the camera can in this case be adapted to provide the distance estimate to the control unit. In such an arrangement, the portable illumination device could be arranged to deliver a powerful flash (e.g. 10 times normal burning power). The electrical interface between the dive light and camera can be wireless or achieved via a waterproof electrical cable. An advantage with such an arrangement, for example in relation to underwater photography, is that it would be possible to take photos or record video without the cumbersome use of color correction filters.

A second aspect of the invention relates to a method for illuminating an object in a medium comprising estimating the distance between an illumination device and the object and adjusting the color distribution depending on said distance estimate, such that light reflected from said object is perceived to have substantially correct color reproduction.

Further features of, and advantages with, the present invention will become apparent when studying the appended claims and the following description. Those skilled in the art realize that different features of the present invention can be combined to create embodiments other than those described in the following.

These and other aspects of the present invention will now be described in more detail, with reference to the appended drawings showing a currently preferred embodiment of the invention.

Figure 1:
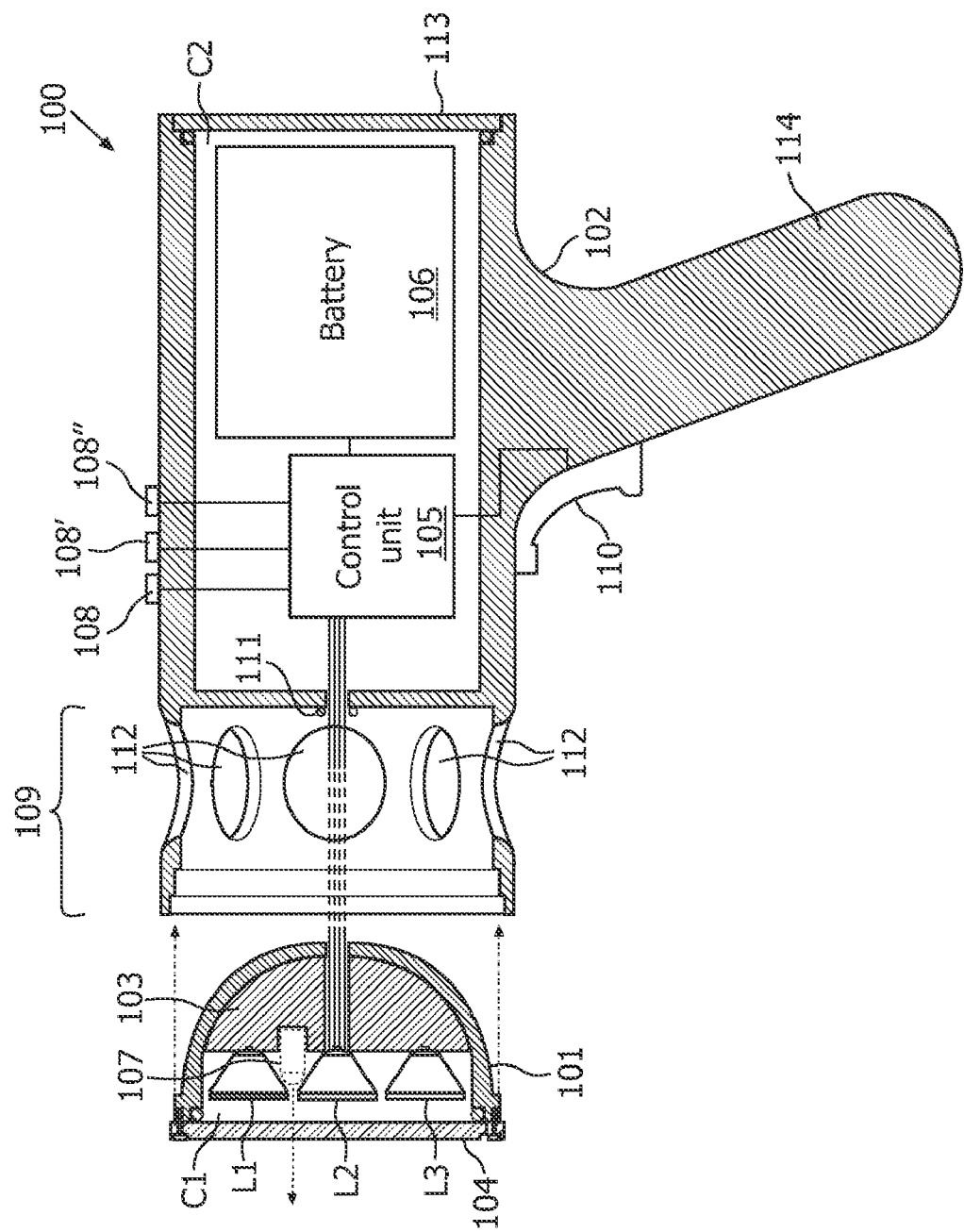
FIG. 1 is a block diagram/cross section of a portable illumination device according to a currently preferred embodiment of the present invention.

In FIG. 1 a block diagram/cross section of a portable illumination device, in this case a dive light 100, according to a currently preferred embodiment of the present invention is shown. The dive light 100 comprises two separate bodies, 101, 102, where the first body 101 constitutes a lighting unit 101 including three differently colored light emitting diodes, $L_1$-$L_3$, each provided with a Total Internal Reflection (TIR) lens, of the color primaries red, green and blue. TIR is a phenomenon where light rays are reflected perfectly from the interface between the guide and the surrounding environment. A person skilled in the art readily understands that more than three light sources might be used, and that other types of light sources can be used, such as for example conventional incandescent light bulbs. The LEDs $L_1$-$L_3$ are arranged onto a bulk volume 103 that is in thermal connection with the exterior surface of the lighting unit 101.

Preferably the bulk volume 103 and the exterior surface of the lighting unit 101 are formed by materials having a high thermal conductivity, such as metal. The material is preferably selected to have resistance to the water (and especially salt water), such as for example a corrosion resistance covering. Aluminum is a preferred material. The lighting unit 101 further has a front covering 104, for example made of Plexiglas (poly methyl methacrylate) or poly carbonate, that is transparent to the light emitted by the LEDs $L_1$-$L_3$. The front covering 104 thereby closes and seals the lighting unit 101 and forms a first waterproof compartment C1.

The second body 102 comprises a control unit 105 and a power supply, such as a battery 106. The battery 106 can be either one of a rechargeable or a disposable battery. In the case that a rechargeable battery is used, the second body 102 can be provided with a waterproof electrical socket for providing a recharge current to the battery 106. In the illustrated embodiment, the control unit 105 is adapted to receive a distance estimate, corresponding to the distance between the dive light 100 and an object to be illuminated, from distance measurement electronics, such as for example a time of flight sensor 107. It would also be possible to use an echo sensor for the purpose of determine the distance to the object. A control button, such a waterproof magnetic switch 110 is furthermore connected to the control unit 105 through which a user can control the activation of the dive light 100.

The control unit 105 is furthermore arranged to receive a water detection signal from a water detector 108, to receive a light absorption characteristics signal from a light absorption sensor 108', and to receive ambient light data from a detection unit 108" adapted to determine the color and intensity of the ambient light. The detectors 108' and 108" provides for an improved accuracy of the color reproduction in the light reflecting from the illuminated object back to the user as the light absorption and the color and intensity of the ambient light is taken into account when adjusting the intensities of the LEDs $L_1$-$L_3$. The second body 102 further has a back covering 113, which thereby closes and seals the second body 102 and forms a second waterproof compartment C2. The second body 102 further comprises a handle 114.

The water detector 108 can be constructed using two contacts separated by approximately 10 mm. Through such a construction the control system would not erroneously think it is still submerged, for example from a water droplet remaining on the detector, resulting in possible damage to the LEDs. The light absorption sensor 108' can be constructed such that light has to travel a sufficient path length through the medium, providing a more accurate light absorption characteristics signal.

The lighting unit 101 is provided with a hole in the middle of the aluminum back part to allow for electrical connection between the lighting unit 101 and the second body 102, connecting the LEDs $L_1$-$L_3$ and the time of flight sensor 107 to the control unit 105. The second body 102 in turn has a similar hole in the middle of its front part. An o-ring 111 is arranged between the lighting unit 101 and the second body 102, which together with a bolt with a hole in the middle pulls the lighting unit 101 and the second body 102 together, fixating the dive light 100, which hence makes the electrical connection waterproof.

As can be seen in FIG. 1, the second body 102 is provided with a sleeve portion 109 having water inlets 112, which provides for effective water cooling of the exterior surface of the lighting unit 101, which becomes warm due to the heat generated from the LEDs $L_1$-$L_3$ which are connected onto the bulk volume 103, which in turn has a thermal connection to the exterior surface of the lighting unit 101. As only a small part of the lighting unit 101 is needed to attach the lighting unit 101 to the second body 102, the design allows for practically the whole exterior of the lighting unit 101 to come in contact with water, providing the most efficient cooling to the LEDs $L_1$-$L_3$. Advantageously, the exterior surface of the lighting unit 101 is directly in contact with the water, providing for a higher efficiency of the LEDs $L_1$-$L_3$. The signal provided to the control unit 105 by the water detector will limit the intensities of the LEDs $L_1$-$L_3$ in the case that no water is detected, such that the LEDs $L_1$-$L_3$ do not overheat due to the lack of water cooling.

In an alternative embodiment of the present invention, the first and the second compartments C1, C2, can be arranged in two separate units. The second unit, comprising the second compartment C2, can in this case for example be arranged onto the divers dive tank, in that way minimizing the size of what the diver holds by the hand. The first unit can in this case for example be arranged as a head mounted dive light.

Figure 2:
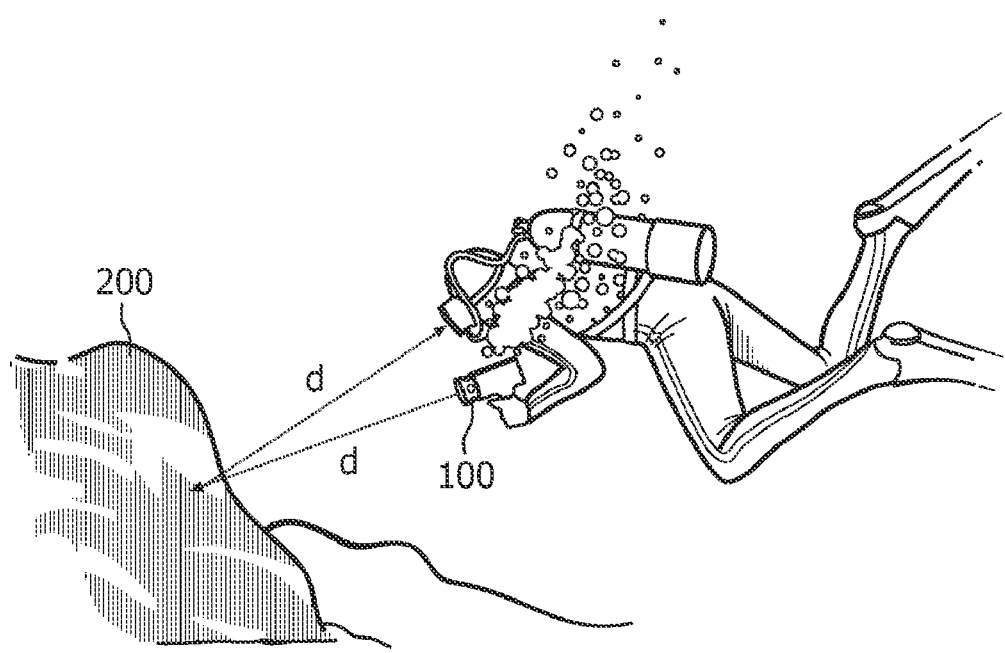
FIG. 2 is an illustration of an illumination device of the present invention used under water.

FIG. 2 illustrates the use of a dive light 100 during underwater SCUBA diving. As a user, through the activation of the magnetic switch 110, indicates the intention to illuminate an object 200, the dive light 100 is activated. Initially, the water detector 108 will detect if the dive light 100 is under water or not, and provide the water detection signal to the control unit 105. If the dive light 100 is above water, the control unit 105 will "turn on" the LEDs $L_1$-$L_3$ at a reduced intensity due to the fact that no water cooling of the lighting unit 101 is provided.

However, if the dive light 100 is under water, the control unit 105 will obtain the light absorption characteristics of the water using the light absorption sensor 108', and the distance to the object 200 to be illuminated using the time of flight sensor 107. The time of flight sensor 107 will measure the time it takes for a short light pulse to travel from the sensor to the object 200 and back, and from that derive the distance to the object 200. As understood by the person skilled in the art, the time it takes for light to travel a distance under water is different from the time it takes for light to travel the same distance above water. A time of flight sensor can use either lasers or LEDs as light sources. LEDs are often less powerful than lasers, limiting their effective distance. Based on the water absorption characteristics and the distance to the object 200 to be illuminated, the control unit 105 will adjust the individual intensities of the LEDs $L_1$-$L_3$ such that the light reflecting from the object is perceived to have substantially correct color reproduction. As understood by the person skilled in the art, it is necessary to take into account the fact that the light has to travel two times the distance to the object: distance measurement=2*d.

The control circuit 105 may include a microprocessor, microcontroller, programmable digital signal processor or another programmable device. The control circuit 105 may also, or instead, include an application specific integrated circuit, a programmable gate array programmable array logic, a programmable logic device, or a digital signal processor. Where the control circuit 105 includes a programmable device such as the microprocessor or microcontroller mentioned above, the processor may further include computer executable code that controls operation of the programmable device.

The control circuit 105 will calculate the color gamut and corresponding color points (i.e. white point), depending on the distance to the object 200 and back to the dive light 100 (i.e. 2*d), for the desired color, e.g. white, and provide signals corresponding to the calculated color points to each of the LEDs $L_1$-$L_3$. The control unit 105 can control the LEDs $L_1$-$L_3$ for example by using pulse width modulation (PWM), which regulates the relative intensities and thereby the mixing ration of the LEDs $L_1$-$L_3$. By controlling the time an LED is turned on and off, and doing so fast enough, the LED will appear to stay on continuously. Since there is less current flowing on average, the LED will appear less bright. It is also possible to control the LEDs $L_1$-$L_3$ by analog adjustment of the amount of current supplied to the LEDs $L_1$-$L_3$.

Figure 3:
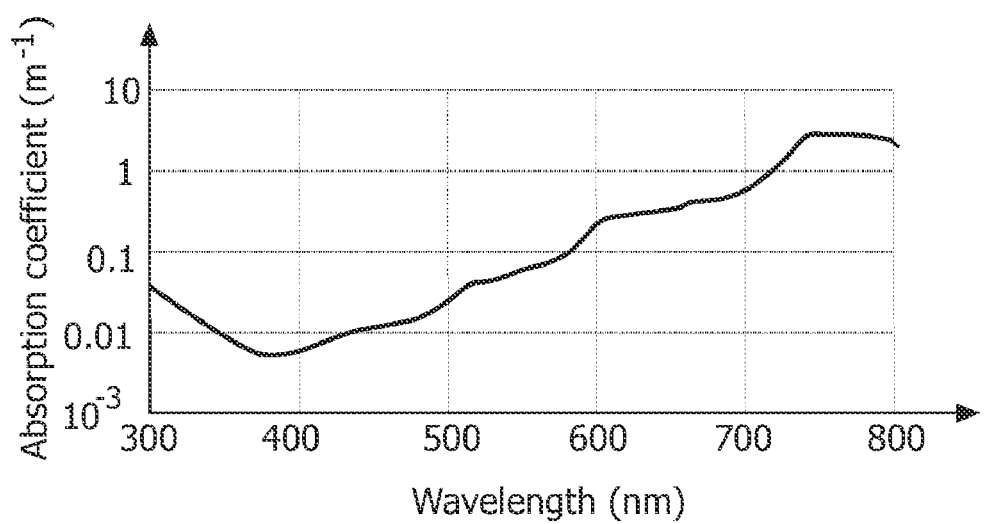
FIG. 3 is a graph illustrating the absorption of light in water.

FIG. 3 further illustrates the absorption of light in water. As can be seen, the amount of absorption varies with wavelength of the incident light, i.e. in regards to the visible spectrum that means that blue light is absorbed least and red light is absorbed most strongly. As been described above, this attenuation is exponential and can be described by the expression:

$$I(d)=I_0 e^{(-\alpha * d)}$$

where I(d) indicates the intensity of the light after traveling a distance d (W/m²), $I_0$ indicates the initial intensity (W/m²), d indicates the distance traveled by the light (m), and α indicates the attenuation coefficient which depend on the wavelength (m$^{-1}$) of the light.

Figure 4:
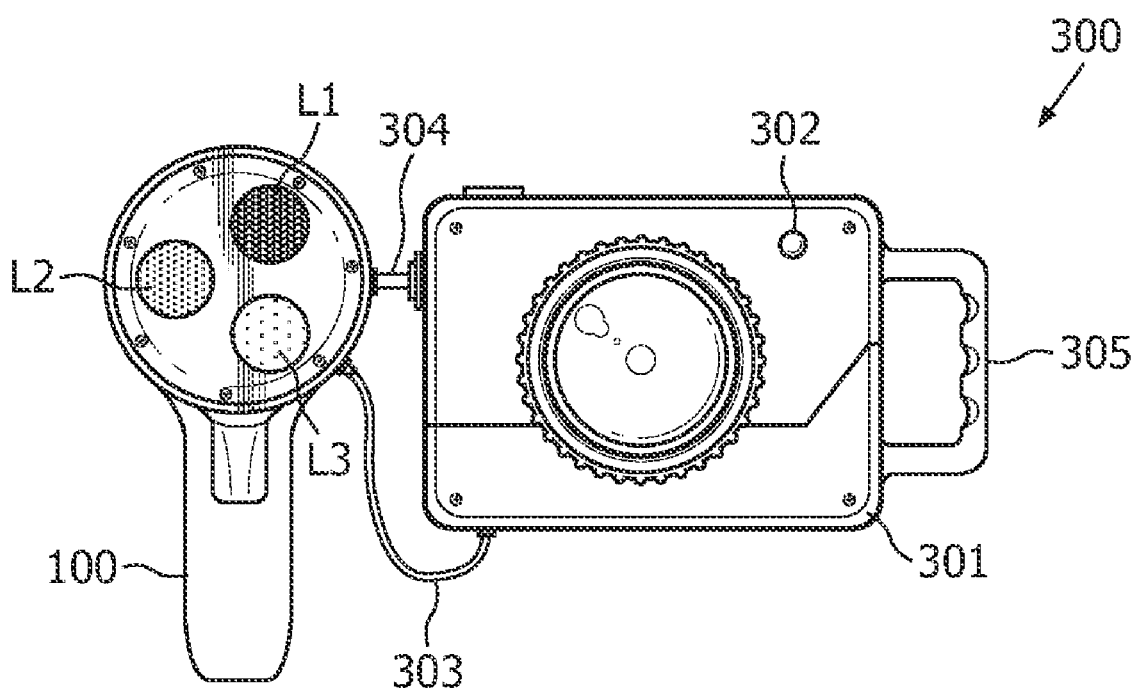
FIG. 4 illustrates a camera arrangement comprising a portable illumination device according to the present invention.

FIG. 4 illustrates a camera arrangement 300 comprising a camera 301 and a portable illumination device 100 according to the present invention. The camera 301 can in this case be one of a photo camera and a video camera. The camera 301 includes a distance/focus sensor 302 arranged to provide a distance to an object such that the lens can be adjusted such that a clear focus is obtained. In a camera arrangement 300 as described, the distance/focus sensor 302 can be adapted to provide the distance measurement to the control unit 105 in the portable illumination device 100. The portable illumination device 100 can in this case be arranged to deliver a powerful flash (e.g. 3-10 times the normal burning power). The electrical interface between the portable illumination device 100 and camera 301 can be wireless or achieved via a waterproof electrical cable 303 as illustrated in FIG. 4. A rod 304 is arranged between the portable illumination device 100 and the camera 301 to allow a user to hold the camera arrangement 300 in one hand using the handle 305. The distance, provided by the rod 304, between the portable illumination device 100 and the camera 301 prevents direct reflections from the portable illumination device 100. A person skilled in the art understands that the camera 301 can be incorporated in the portable illumination device 100. An advantage with a camera arrangement 300 as illustrated in FIG. 4, for example in relation to underwater photography, is that it would be possible to take photos or record video without the cumbersome use of color correction filters.

The person skilled in the art realizes that the present invention by no means is limited to the preferred embodiments described above. On the contrary, many modifications and variations are possible within the scope of the appended claims.

For example, it is possible to, in regards to a dive light, further adapt the portable illumination device to comprise a dispelling light function to repel aggressive and/or dangerous fish types. Such a function would generally include a "panic" button on the dive light that may be activated by the user in the case that a dangerous fish, such as a shark, comes close to the user. The activation of the panic button will in this case provide a panic signal that is received by the control unit, which in turn will turn ON and OFF the LEDs according to a predefined pattern. Such a fish dispelling pattern is known in the art.

Additionally, a safety function can be provided with the portable illumination device which switches off the main illumination function and activates a single safety LED which provides emergency light when the battery voltage drops below a predefined value. This safety function can furthermore be used for communication between a plurality of users, such as by means of an "Emergency" signaling function (flickering with an unusual frequency, which for example might be the same as in the dispelling mode) or an SOS signaling function.

The invention claimed is:

1. A portable illumination device for illuminating an object through a medium, the medium having an absorption coefficient and being able to absorb a portion of the visible light spectrum, said illumination device comprising:

a lighting unit including at least two differently colored light sources for emitting light having a color distribution; and a control unit for adjusting said color distribution, wherein said control unit is adapted to:
 receive a distance estimate corresponding to a distance between said illumination device and said object; and
 adjust said color distribution depending on said distance estimate, such that light reflected from said object is perceived to have substantially correct color reproduction.

2. The portable illumination device according to claim 1, wherein said adjustment is further based on said absorption coefficient.

3. The portable illumination device according to claim 1, wherein said control unit is adapted to adjust said color distribution by adjusting relative intensities of said light sources.

4. The portable illumination device according to claim 1, wherein said at least two differently colored light sources at least one red light source.

5. The portable illumination device according to claim 4, wherein said correct color reproduction is achieved by adjusting the amount of light emitted by said at least one red light source.

6. The portable illumination device according to claim 1, wherein said lighting unit comprises at least three differently colored light sources including at least one red light source, at least one green light source, and at least one blue light source.

7. The portable illumination device according to claim 1, wherein said light sources are selected from a group comprising LEDs, OLEDs, PLEDs, inorganic LEDs, CCFLs, HCFLs, plasma lamps.

8. The portable illumination device according to claim 1, wherein said illumination device further comprises a user interface arranged to allow a user to provide said distance estimate.

9. The portable illumination device of claim 8, wherein the user interface includes a distance selector for selecting the estimated distance from predefined distance estimates.

10. The portable illumination device according to claim 1, wherein said illumination device further comprises distance measuring electronics adapted to provide said distance estimate.

11. The portable illumination device according to claim 1, wherein said illumination device is an underwater dive light, wherein said lighting unit constitutes a first waterproof compartment, wherein said control unit is arranged in a second waterproof compartment having an electrical connection to said first compartment, and wherein said first compartment and said second compartment are arranged relatively to each other such that, in use, water is brought into contact with an exterior surface of said first compartment, such that heat generated by said light sources is effectively absorbed by the water.

12. The portable illumination device according to claim 11, wherein said exterior surface of said first compartment is formed by a material having a high thermal conductivity, and wherein said light sources are arranged in thermal connection with said material.

13. The portable illumination device of claim 12, wherein the material comprises a metal.

14. The portable illumination device according to claim 11, wherein said illumination device further comprise a water detector adapted to provide a water detection signal, and wherein said control unit is further adapted to:
 receive said water detection signal; and
 adjust said color distribution based on said water detection signal.

15. The portable illumination device according to claim 11, wherein said illumination device further comprises light absorption characteristics electronics adapted to provide wavelength dependent absorption data of the surrounding medium, and wherein said control unit is further adapted to:
 receive said absorption data; and
 adjust said color distribution based on said absorption data.

16. The portable illumination device according to claim 11, wherein said illumination device further comprises a detection unit determine ambient light data including color and intensity of ambient light, and wherein said control unit is further adapted to:
 receive said ambient light data; and
 adjust said color distribution based on said ambient light data.

17. The portable illumination device of claim 1, further comprising a water detector for detecting water, wherein the control unit is further adapted to limit intensities of the light emitted from the light sources when no water is detected by the water detector.

18. The portable illumination device of claim 1, wherein the control unit is further adapted to turn on/off the at least two differently colored light sources in a panic mode, and to turn on/off one of the at least two differently colored light sources in an emergency mode.

19. A camera arrangement, comprising:
 a camera comprising a distance/focus sensor adapted to provide a distance estimate; and
 a portable illumination device comprising:
 a lighting unit including at least two differently colored light sources for emitting light having a color distribution; and
 a control unit for adjusting the color distribution, wherein the control unit is adapted to:
 receive the distance estimate corresponding to a distance between the illumination device and an object; and
 adjust the color distribution depending on the distance estimate.

20. A method for illuminating an object through a medium, the medium having an absorption coefficient and being able to absorb a portion of the visible light spectrum, using a portable illumination device having a lighting unit including at least two differently colored light sources for emitting light having a color distribution; and a control unit for adjusting said color distribution, said method comprising the acts of:
 estimating a distance between said illumination device and said object; and
 adjusting said color distribution depending on said distance estimation, such that light reflected from said object is perceived to have substantially correct color reproduction.

21. The method according to claim 20, wherein said adjustment is further based on said absorption coefficient.

22. The method according to claim 20, wherein said color distribution is adjusted by adjusting relative intensities of said light sources.

23. The method according to claim 20, wherein said estimation is performed using distance measurement electronics.

24. The method according to claim 23, wherein said estimation is performed using a distance/focus sensor of a camera, which is used to acquire an image of said object.

* * * * *